United States Patent [19]
Gombocz et al.

[11] Patent Number: 5,104,512
[45] Date of Patent: Apr. 14, 1992

[54] GEL ELECTROPHORESIS SYSTEM

[75] Inventors: Erich A. Gombocz, Vienna, Austria; Robert R. Clappier, Los Altos, Calif.; Wilhem Kerth, Vienna, Austria; David H. Rammler, Woodside; Alex Roth, Foster City, both of Calif.

[73] Assignee: Labintelligence, Inc., Menlo Park, Calif.

[21] Appl. No.: 522,325

[22] Filed: May 14, 1990

[51] Int. Cl.$^5$ .................. B01D 61/42; C25D 13/00; C25B 1/00
[52] U.S. Cl. ............................ 204/299 R; 204/182.8
[58] Field of Search ................ 204/182.8, 299 R

[56] References Cited

U.S. PATENT DOCUMENTS

| | | | |
|---|---|---|---|
| 4,306,956 | 12/1981 | de Castro et al. | 204/299 R |
| 4,657,655 | 4/1987 | Smoot et al. | 204/299 R |
| 4,810,348 | 3/1989 | Sarrine et al. | 204/182.8 |

Primary Examiner—John Niebling
Assistant Examiner—Caroline Koestner
Attorney, Agent, or Firm—Bertram I. Rowland

[57] ABSTRACT

An electrophoretic system is provided which allows for carrying out electrophoresis while monitoring and regulating the temperature and the electrical field gradient in the gel. In addition, photometric monitoring is provided so as to monitor the progress of the electrophoretic separation and vary conditions to change the progress as desired. A computer is employed which receives the signals from the electrophoretic and photometric apparatuses and regulates temperature and voltage to either maintain conditions, or change the conditions to vary the progress of the electrophoresis. Gel molds are provided for forming the lanes in a gel plate, as well as a light module, for reading the bands present in the gel lanes with the photometer.

11 Claims, 8 Drawing Sheets

FIG.—1

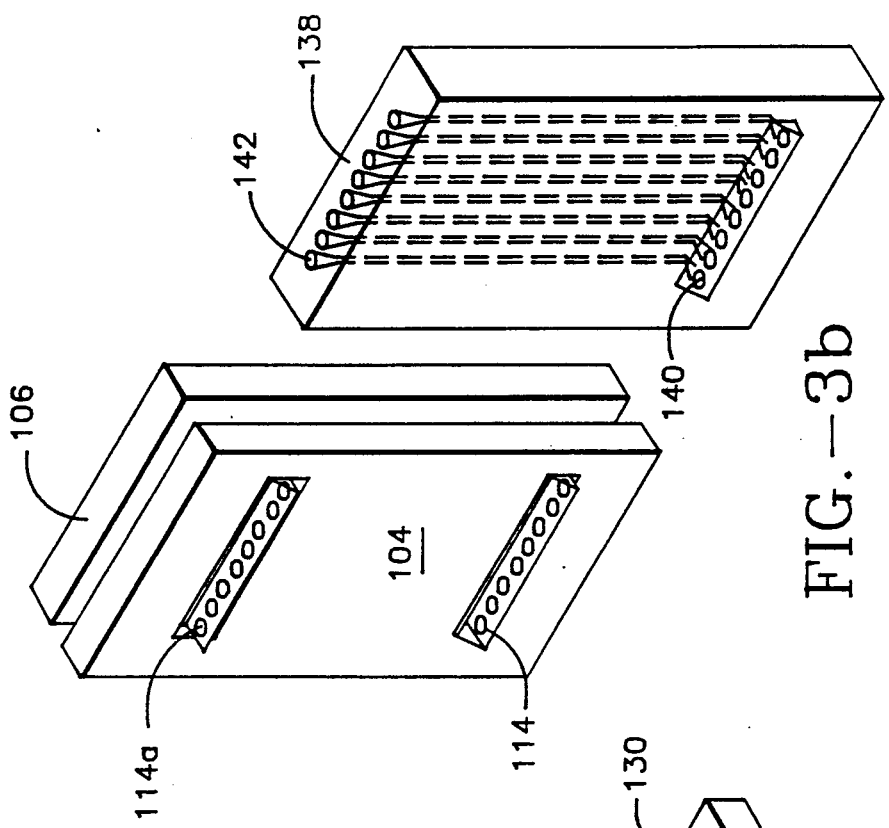
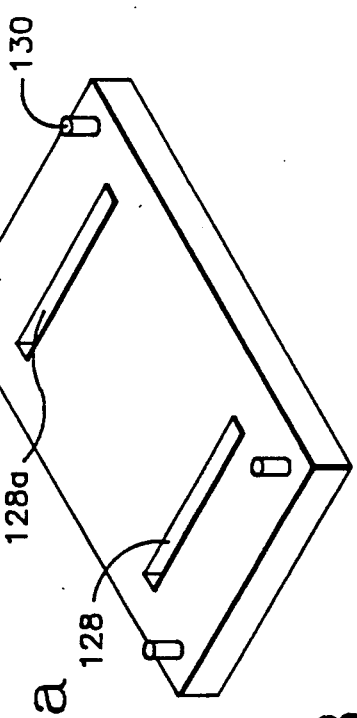
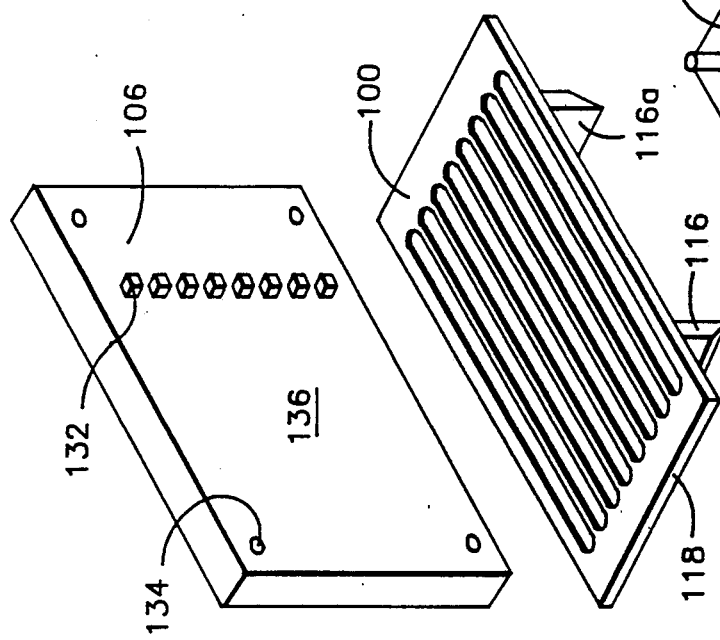
FIG.—3b
FIG.—3a
FIG.—3

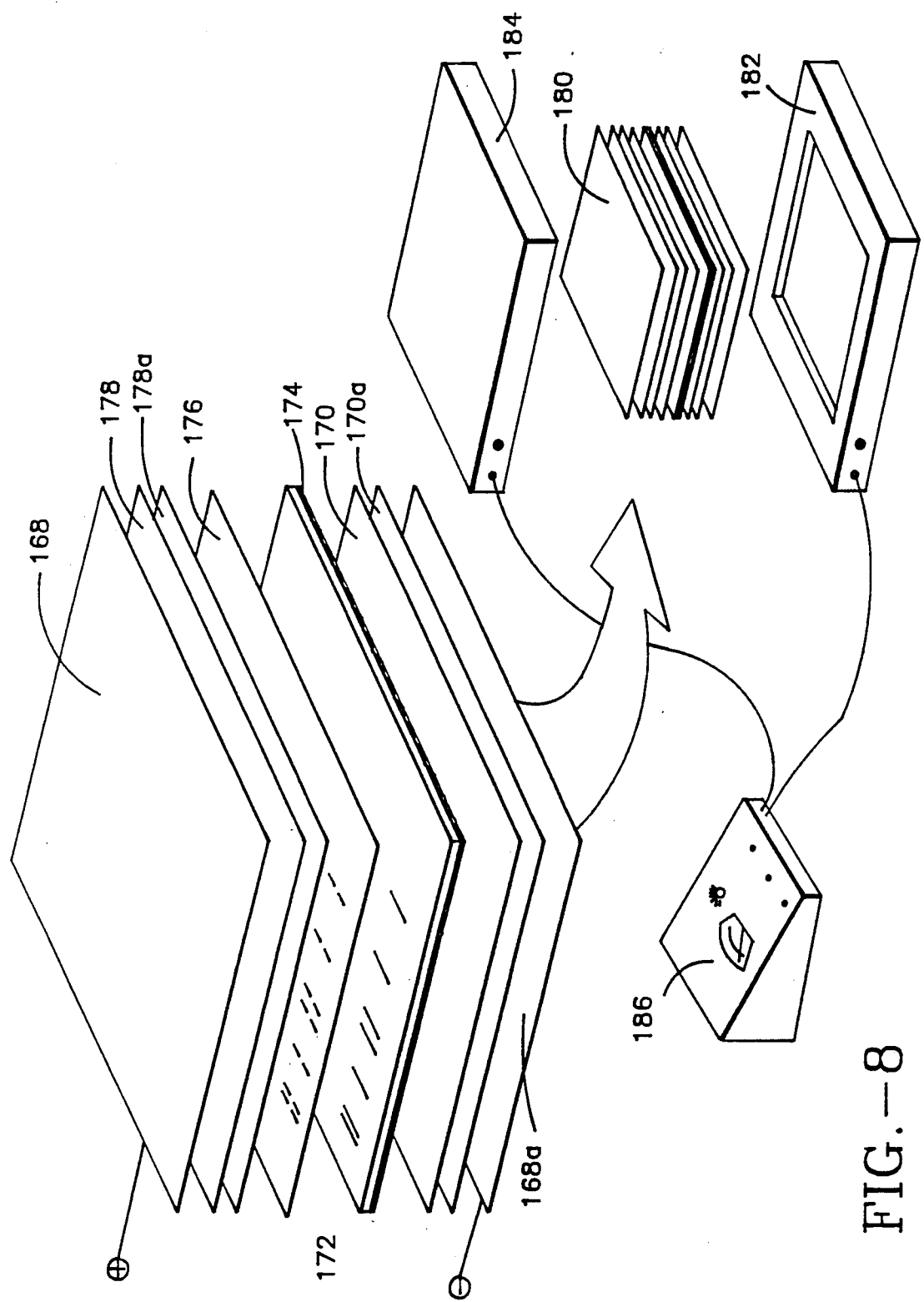
FIG.—8

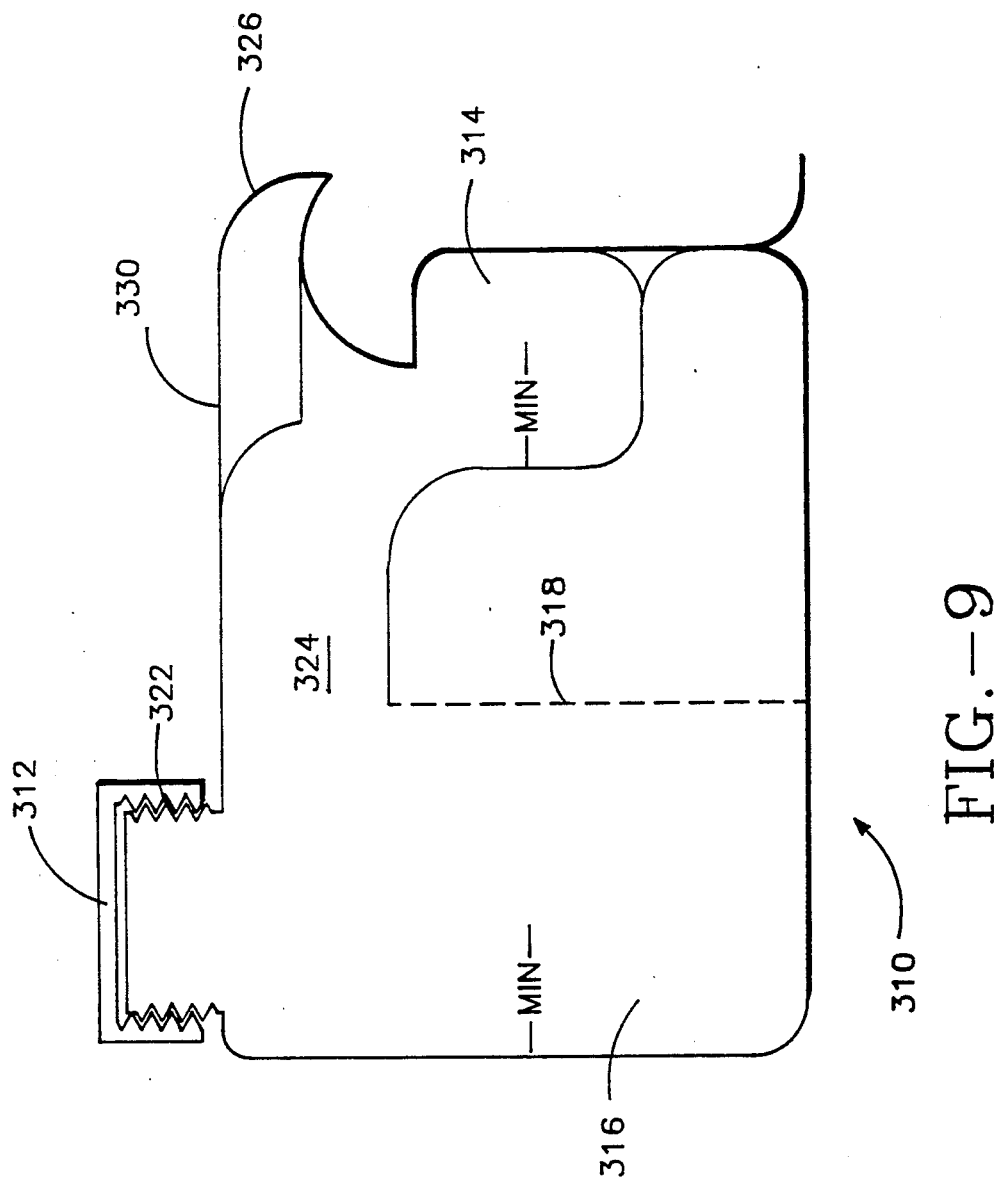
FIG.—9

GEL ELECTROPHORESIS SYSTEM

TECHNICAL FIELD

The field of this invention is gel electrophoresis.

BACKGROUND

With the huge expansion in biotechnology, gel electrophoresis has become an indispensable tool. The ability to separate nucleic acid fragments and proteins by means of size, shape and charge has added numerous opportunities to identify specific compounds, indicate purity, and allow for isolation of a compound in relatively pure form. By being able to change the conditions under which one carries out the electrophoresis, one can determine many characteristics of the compounds in the sample.

A variety of new techniques are predicated on the use of gel electrophoresis in an efficient and convenient way. Restriction fragment length polymorphisms is one application where one can perform genetic diagnosis by means of a genomic DNA sample. This technique may also be used in forensic medicine to identify the source of nucleic acids. Gel electrophoresis may also be used to identify a compound, by separation of a complex mixture and then by using markers, such as antibodies, or the like. Electrophoresis is used in conjunction with transfer to a membrane such as Southern, Northern, and Western blotting, or other techniques involving transfer of the separated sample to a different substrate.

While much of the power of gel electrophoresis as a tool in identification and separation is realized, there are still many shortcomings. Apparatuses tend to be relatively large and cumbersome. Comparisons from samples or runs and particularly from different laboratories are very difficult since conditions of the electrophoresis vary and regulation and monitoring of the conditions is not available or unreliable. Thus, one frequently gets wide variation in determinations of molecular weight, as well as the properties of the sample components. Therefore, it has been very difficult to make comparisons from one run to another, no less from one laboratory to another. Also, the gel electrophoretic apparatus usually does not prevent the sample from running off the gel, nor does it provide assurance that the sample has had sufficient time for a reasonable separation. Thus, substantial improvements in presently available equipment is desirable in order to obtain a satisfactory electrophoretic separation.

There is substantial interest in being able to provide electrophoretic systems which can be substantially automated, assure directly comparative results, and provide economies in the use of electrophoresis.

RELEVANT LITERATURE

References include Schafer-Nielsen, *Electrophoresis* 1987, 8, 20; Szewaczyk et al., ibid 1987, 8, 25; Gill et al., ibid 1987, 8, 38; Demeulemester et al., ibid 1987, 8, 71; Blum, et al. ibid 1987, 8, 93; Albaugh et al., ibid 1987, 8, 140; Serwer and Hayes, ibid 1987, 8, 244; Zapolski et al, ibid 1987, 8, 255; Tretz et al., ibid 1987, 8, 271; Breborowicz et al., ibid 1987, 8, 313; Pascali et al., ibid 1987, 8, 371; Orban et al., ibid 1987, 8, 465; Frey et al., ibid 1986, 7, 28; Carpenter et al., ibid 1986, 7, 221; Tretz et al., ibid 1986, 7, 241; Lamben et al., ibid 1986, 7, 342; Foret et al., ibid 1986, 7, 430; Prin et al., ibid 1985, 6, 268; Lockshin, ibid 1985, 6, 282; Mosher and Thormann, ibid 1985, 6, b/77; Rhalem and Pery, ibid 1985, 6, 564.

SUMMARY OF THE INVENTION

A gel electrophoresis system is provided comprising a gel electrophoresis apparatus having a gel slab supporting platform, buffer wells, electrodes for maintaining an electrical field across the gel, a pair of electrodes to monitor the voltage in the gel, and temperature monitoring and controlling means for controlling the temperature in the gel. Ancillary to the gel separation slab is a spectrophotometer means for monitoring the movement of fractions in the gel. Also provided is an electrophoretic concentrator or stacking gel to concentrate fractions present in the sample prior to applying the sample to the gel.

In addition, the system includes a gel holder and forms for preparing gels, particularly as a plurality of individual lanes.

The progress of an electrophoresis is monitored as to temperature of the gel, electrical gradient across the gel, progress of individual bands and the separation between bands, where a constant temperature and field may be maintained or varied depending upon the purpose of the electrophoresis.

The system provides for accurate reproducible separation of nucleic acids, proteins, saccharides, particles, such as virus particles, and determination of the size and characteristics of individuals molecules and particles.

DESCRIPTION OF THE DRAWINGS

FIGS. 3, 3a and 3b are diagrammatic perspective view of the gel casting components;

FIG. 8 is a perspective view of components for blotting the gel;

FIG. 9 is a perspective view of a buffer diluter container.

DESCRIPTION OF THE SPECIFIC EMBODIMENTS

Figure 1:
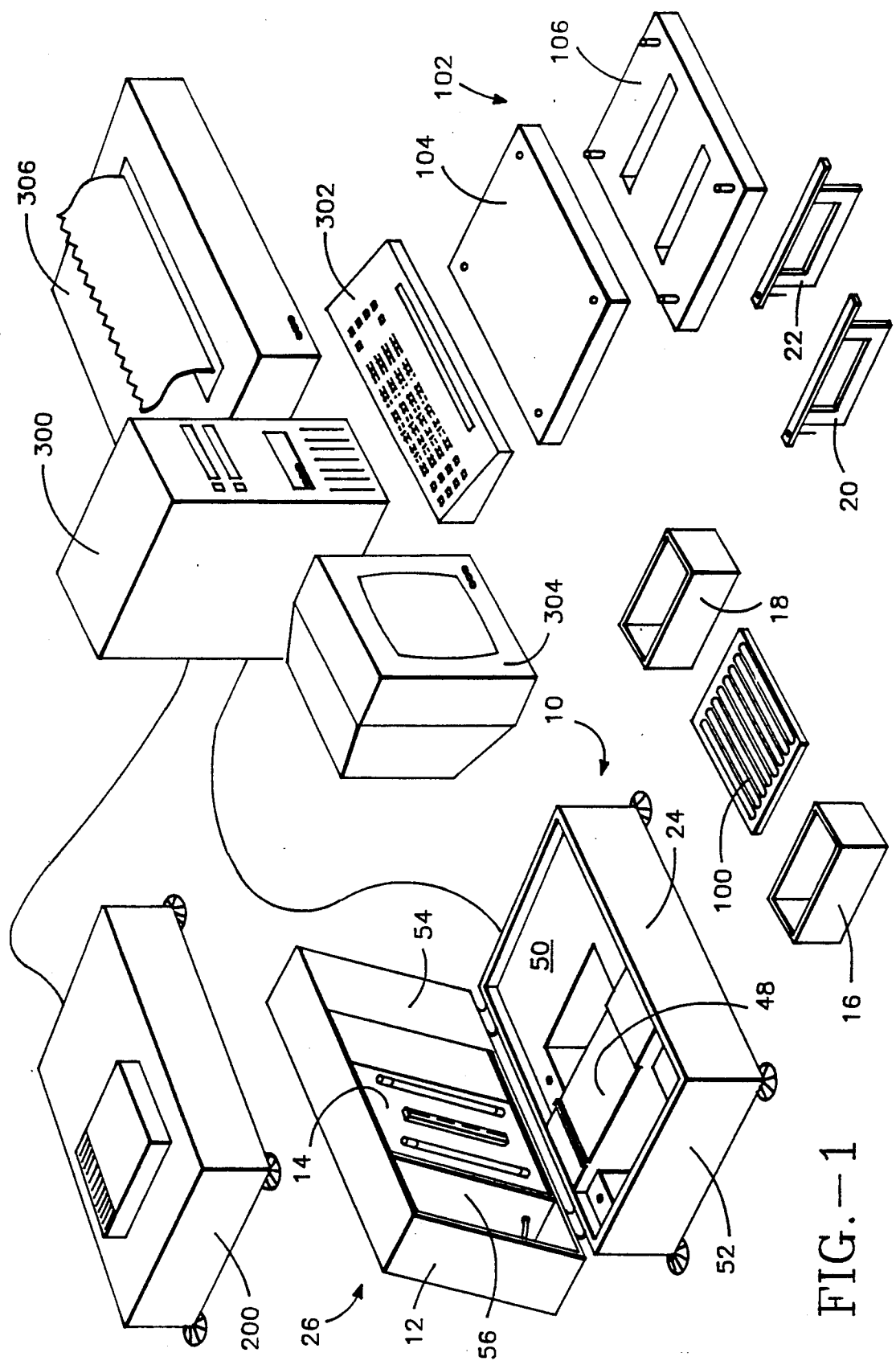
FIG. 1 is a diagrammatic representation of the electrophoresis system according to this invention.

An integrated gel electrophoresis system is provided which allows for controlled reproducible separation of macromolecules, including nucleic acids, proteins, saccharides, and combinations thereof. The system provides for monitoring and regulating a number of variables associated with the gel electrophoresis. By monitoring the status of each of a plurality of variables associated with the gel electrophoresis and regulating the conditions of the gel electrophoresis, reproducible band patterns can be achieved, and conditions standardized or varied depending upon the particular needs of the electrophoresis. Among the variables monitored are the voltage gradient in the gel, the temperature of the gel, and the movement of one or more bands in the gel. By insuring a stable temperature and electrical field in the gel, the molecules in the sample move in a reproducible manner through the gel. By monitoring the progress of the movement of the bands, one can increase or decrease the voltage gradient in the field to increase or decrease the rate of movement of the molecules or terminate the electrophoresis, when a desired level of separation or desired distance traveled has been obtained.

By providing for a cooling platform to support the gel and providing for good heat transfer between the platform and the gel, the temperature in the gel may be maintained within a relatively narrow range. One or more temperature sensors, e.g., thermocouples or integrated circuit temperature sensors, may be employed so as to monitor the temperature at the surface of the platform and/or in the gel so that information may be continuously fed to a monitor for regulating the temperature in the gel.

The voltage gradient in the gel may be monitored by having two or more electrodes distinct from the electrodes which provide the voltage gradient across the gel. These additional electrodes would be spaced apart across a substantial portion of the gel, usually greater than about 60%, preferably 70%, of the length of the gel. The electrodes would be in contact with the gel, conveniently at an edge, so as to be able to determine the voltage drop between the two electrodes and across the gel in the direction of the field. By monitoring the actual voltage in the gel, variations in the field in the gel may be regulated to maintain a constant field. By maintaining a constant field and a constant temperature, the significant conditions controlling the movement of molecules in the gel can be maintained, so that the molecules move in a regulated and reproducible fashion.

The separation path length starts at the sample application position. The separation distance is usually at least about 5 cm, preferably at least about 10 cm, which is about 75% of the total gel distance. The remaining portion of the gel, from the catholyte to the sample application position, will be present for stacking, unless stacking is obtained by another method.

The progress of the electrophoresis is also monitored, so that the progress of the bands is determined. The progress is monitored spectrophotometrically, where the absorption or fluorescence, normally resulting from staining of the molecules present in the gel, may be determined. Detection of the bands may be as a result of endogenous spectrophotometric properties of the molecules or as a result of the presence of dyes in the gel or band which may interact with the molecules to provide for variation in spectrophotometric properties associated with the presence of the molecules in the gel. By monitoring the progress of the electrophoresis, opportunities exist to vary the other variables, such as temperature and electrical field gradient, to reduce or increase the rate of movement of the molecules in the gel. Thus, one can increase or decrease the rate at which the electrophoresis is carried out or stop the electrophoresis as desired. Rather than having to wait until a marker has moved to some predetermined position on the gel or has gone off the gel, one can terminate the electrophoresis at any appropriate time.

The repetitive monitoring of temperature and electrical field in conjunction with the progress of the electrophoresis, with concurrent regulation of temperature and electrical field, provides the capability to control the conditions under which the electrophoresis is carried out in a reproducible and comparable manner. By providing comparable conditions with a comparable apparatus, one can be assured that comparable results will be obtained, whether at the same laboratory or a different laboratory. The significance of being able to compare results, means that one can have greater certainty whether the same or different materials are involved, as well as the significance of the characteristics of the sample which are determined from the electrophoresis.

By monitoring the variables associated with the electrophoresis, numerous other additional advantages are achievable. For example, one can use soft gels which allow for relatively rapid migration of sample components, since the movement of the components may be monitored. In this way, very large particles and molecules may be separated and characterized. One may also provide for Ferguson plots, by having a plurality of lanes at different gel concentrations resulting in different sizes of the gel matrix. The reproducibility of the plot allows for comparison between components in different samples and provides an additional characteristic for identification of a particular composition or molecule. Other advantages will also be apparent as the system is described further.

The system comprises the gel module which has a temperature regulated platform on which the gel plate sits, buffer well containers which may be fixed or removable, and electrodes, which may be fixed or removable for placing in the buffer wells to provide the electrical field in the gel. The gel module also has a pair of electrodes for fitting into the gel holder and determining the electrical field gradient in the gel. In addition the gel module has electrical connections for powering the cooling system and electrodes for producing the electrical field gradient in the gel and connecting the cooling system, the field gradient electrodes and the gel monitoring electrodes to a monitoring and regulating means for controlling the variables associated with the temperature and electrical field in the gel. A removable electroluminescent plate may be provided for mounting on the cooling plate, which would allow for reading the gel, after the electrophoresis has been finished and the gel stained or the nucleic acid labeled.

Removably mounted on the gel module is a photometer module, which provides an excitation light source and a spectrophotometer which detects zone fluorescence or light absorption in the gel. Controlled motor-driven mechanical means are provided for moving the spectrophotometer and excitation light source over the surface of the gel to scan the gel. The light emitted from the particle zones in the gel is detected and the resulting signal transmitted to the monitoring and regulating means for controlling the progress of the electrophoresis. Means are provided for locating the position of the photometer module in relation to the gel.

In addition, a light box may be provided over which the photometer module fits, where the gel holder may be scanned spectrophotometrically for light absorption or emission. The light box may be in addition to or in lieu of an electroluminescent panel.

The monitoring and regulating means is conveniently a computer with appropriate software for regulating the conditions and progress of the electrophoresis. Optionally included will be a keyboard for interacting with the computer and a monitor for visually monitoring the conditions and progress of the electrophoresis.

For convenience, gel molds and plates for holding the gel are provided, where the gel plates are designed for accommodation with the gel platform and buffer wells and for receiving the monitoring electrodes.

Turning now to the drawings, FIG. 1 is a diagrammatic representation of the various components of the system of which the electrophoresis device 10 is the central element. The electrophoresis device 10 has a gel module 24 with a cover 12 which houses a photometer 14 providing the separable photometer module 26. Used in conjunction with the gel module 24 are removable buffer wells 16 and 18 and removable electrode holders 20 and 22.

The gels for the electrophoresis may be formed in gel plate 100 using gel mold 102 having a top plate 104 and a lower plate 106.

A light box 200 is optionally provided for reading gels in conjunction with the photometer module 26, which can fit over the light box 200.

Signals from the gel module 24 and the photometer module 26 may be fed to a computer and data storage device 300, fitted with keyboard 302, CRT 304 and printer 306. By providing for an interactive relationship between the computer and data storage device, the gel module 24 and the photometer module 26, one can monitor the course of the electrophoresis and vary or maintain conditions as desired.

Figure 2:
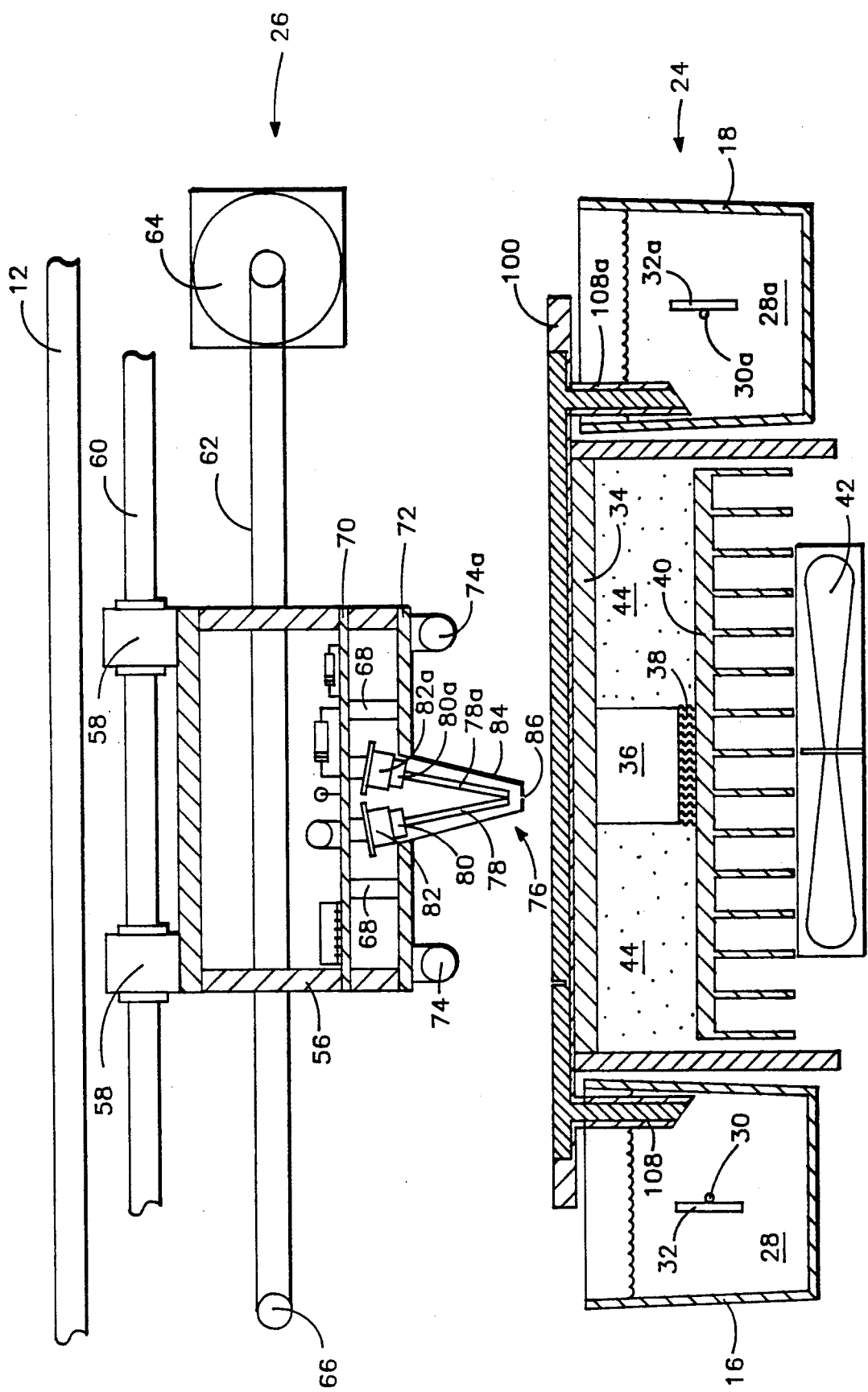
FIG. 2 is a diagrammatic sectional elevational view of the gel module.

In FIG. 2 the gel and spectrophotometer modules are depicted, where the gel module 24 is the lower component and the photometer 26 is the upper component.

The gel module 24 will have a first buffer solution well 16 containing buffer solution 28, electrode 30 and detachable electrode support 32. Similarly, buffer well 18 will include buffer 28a, electrode 30a and detachable electrode support 32a. The electrode support may be selected to interact with a detector to allow for continuous monitoring of the ionic levels of the buffer solutions. Thus, when the buffer solution 28 drops below a predetermined level of ionic strength level, a pump, not shown, can be activated to replenish the buffer to a predetermined ionic strength level by adding a concentrated solution. Various ion responsive electrodes may be employed for monitoring buffer concentration. In this way, the buffer may be maintained so as to avoid any interruption of the electrophoresis as a result of depletion of the buffer below a predetermined level.

The gel module 24 has a temperature control system comprising a cooling plate 34 mounted on a heat transfer block 36, which is in turn in heat transfer relationship with a cooling device, e.g., a Peltier device 38. The heat produced by the cooling device is transferred to the atmosphere by means of a finned heat sink device 40 and fan 42. The heat transfer block 36 and cooling device 38 are surrounded by insulation 44, where the various components of the temperature control system are housed within housing 46. The buffer wells 16 and 18 and the temperature control system 48 (see FIG. 1) are supported by platform 50 of electrical circuitry housing 52.

Gel plate 100 is seated on aluminum cooling plate 34 and has legs 108 and 108a extending into buffer solutions 28 and 28a respectively.

The photometer module 26 comprises gel module cover 12 and photometer 14, as shown in FIG. 1. The photometer module has recessed well 54 for withdrawing the carriage 56 to inhibit any interaction between the gel plate 100 and the photometer 14. Carriage 56 is mounted on linear rod bearings 58 which ride on guide rod 60. Movement of the carriage is controlled by belt 62 which is driven by stepping motor 64, where the belt passes over idle pulley 66. By knowing the position from which the carriage initiated, one can count the steps of stepping motor to determine the carriage position at any time. Alternatively, the stepping motor 64 may be connected to a monitoring device, e.g., a potentiometer, so that the location of the photometer 14 in relation to the gel can be monitored and the location of the bands in the gel determined. Supports 68 support circuit board 70, and in turn are supported by floor 72 of carriage 56.

A blacklight bulb 74 serves as a light source for activating fluorescent components in the gel. A second black light bulb 74a may be employed to insure sufficient light intensity across the region absorbed by light sensing unit 76.

Light sensing unit 76 has two fiber optic pipes 78 and 78a. The fiber optic pipes 78 and 78a feed light from the gel to color filter disks 80 and 80a respectively. Individual fiber optic pipe pairs are provided for each lane to be observed, where the pipes may be to the same or different photodetectors. Means may be provided for individually sampling each pair of pipes. The color filter disks 80 and 80a have wave length absorption ranges of about 400-600 nm and 500-700 nm, where the transmission increases at higher wavelengths for the former and decreases for the latter. By appropriate Fourier analysis of the differences in the light absorbed and detected by photodetectors 82 and 82a respectively, one can measure the light at various wave lengths within a relatively narrow range of about 400 nm to 700 nm. The Fourier analysis is done by overlay of the transformed polynomial derived according to the absorption profiles of the two filters used in the separate detector channels. Thus, using discs from plastic filter sheets, a color discrimination resolution of TM 50 nm is achieved.

As described, by having only two photodetectors and two filters, one can detect fluorescence at different wave length ranges over a broad spectrum of fluorescent light. A conical or triangular cross-section enclosure 84 encloses the fiber optic pipes 78 so as to direct light to the fiber optic pipes 78 through aperture 86. The carriage 56 can move the enclosure 84 with aperture 86 across the gel plate 100, where the blacklight bulbs will photoactivate fluorescent compounds present in the gel.

By employing light sources having a broad wave length spectrum which encompasses the absorption maximum of fluorescers present in the gel, where the fluorescence occurs in relation to the movement of sample components in the gel, the component bands will fluoresce and the fluorescence will be detected by the photodetectors 82 and 82a. Where different components may provide for different fluorescent wave lengths, the ability to detect the presence of the different wave lengths, allows for a determination of how far each component has progressed. The photometer may be maintained in a single position, so as to detect the arrival or passage of one or more components past the position of the photometer, or may be repeatedly traversed across the gel plate, so as to repetitively monitor the progress of the electrophoresis.

The cooling plate 34 may be coated with a reflective material or a dark material, depending upon whether it is desired to reflect light from the gel or to absorb any light directed toward the cooling plate 34. A light reflective background provides greater levels of excitation. The choice will depend upon such considerations as the Stokes shift of the fluorescer present in the gel, the nature of the fluorescer, for example, where there is a significant time lag between absorption and electron excitation and fluorescence, the specific wave length of the excitation light and the fluorescent light, the fluorescence efficiency, and the like.

Figure 4:
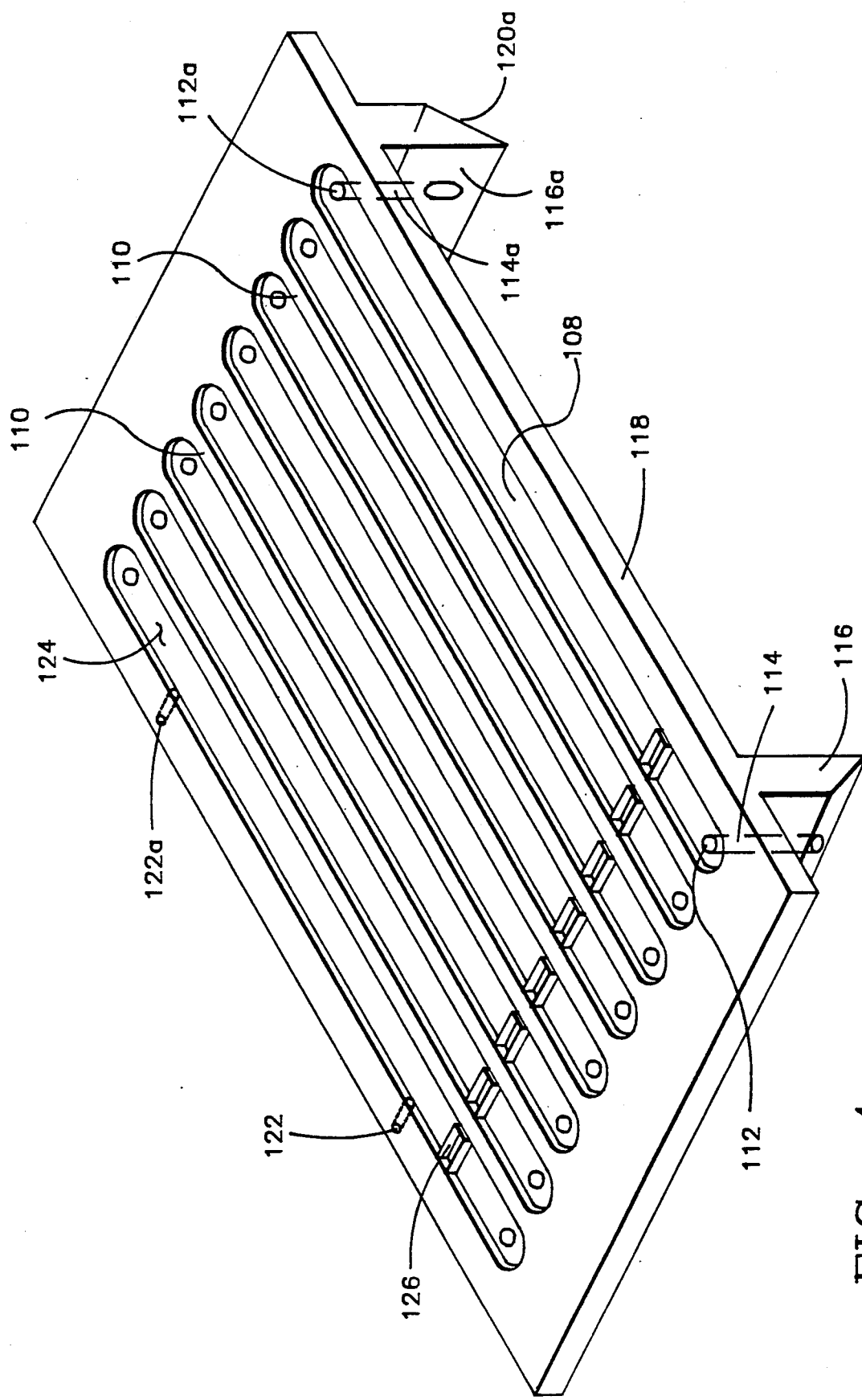
FIG. 4 is a perspective view of a gel plate according to this invention.
Figure 5:
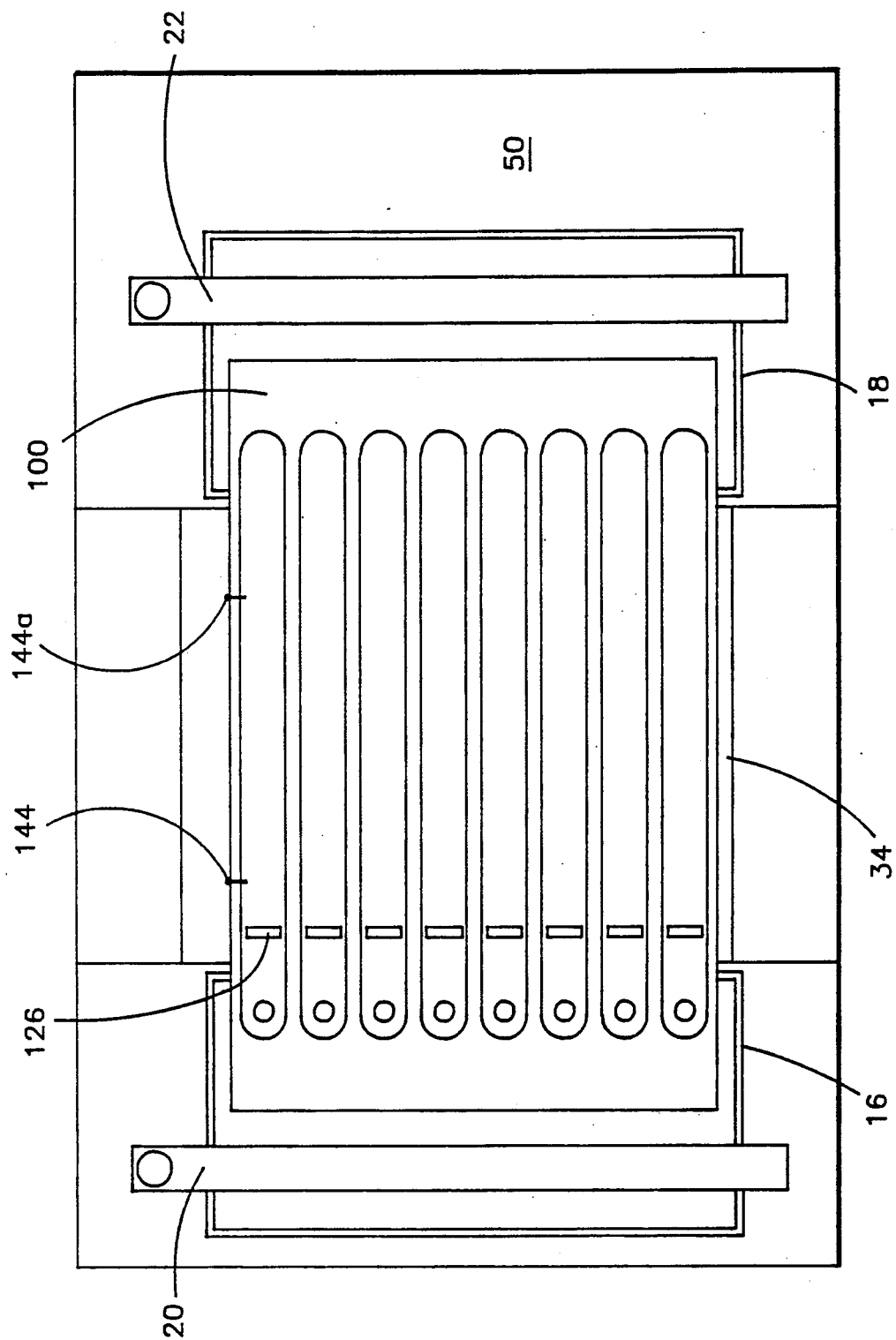
FIG. 5 is a plan view of the gel plate in the gel module.
Figure 7:
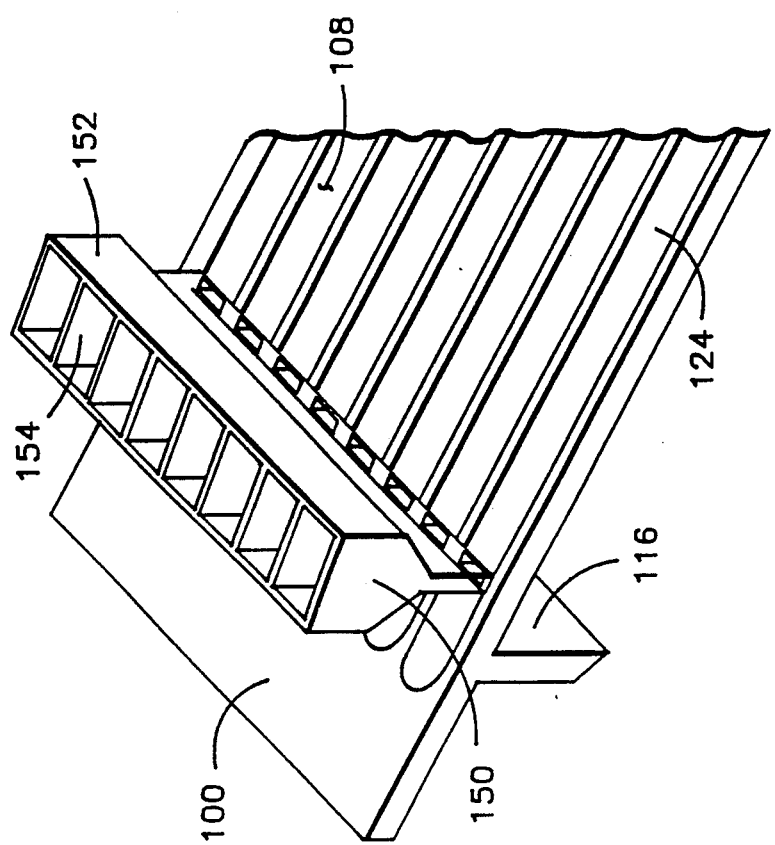
FIG. 7 is a perspective view of the electrophoretic concentrator as applied to a gel plate.

In accordance with the subject invention, plates are designed for use with the gel module. The gel plate 100 is depicted in FIGS. 3, 4 and 5, where FIG. 3 illustrates the gel mold in its opened and closed forms. The gel mold 102 has a bottom plate 104 which is desirably made of transparent plastic, so that one can observe the gel plate 100 for air bubble entrapment and also to allow for transmission of light. The gel plate 100 has a plurality of lanes 108 separated by dividers 110. Proximal to each end of lanes 108 are orifices 112 and 112a which communicate with channels 114 and 114a, respectively. The channels may conveniently be produced in plastic blocks 116 and 116a, fixedly attached in registry with the lanes to upper plate 118 which comprises the lanes 108. The channels 114 and 114a are in register with orifices 112 and 112a, respectively. The bottom of the plastic blocks 116 and 116a have a beveled bottom 120 and 120a at an acute angle. The beveled bottoms protect the gel from contaminating surfaces, minimize air bubble blockage at the interface with buffer, as well as maximizing gel and buffer interface.

The upper plate 118 will normally be a clear plastic, where the bottom of the plate may be mirrored or blackened or left clear, allowing for cooling plate 34 to provide the appropriate light absorption or reflection characteristics. Electrode receiving channels 122 and 122a are provided for introduction of electrodes which contact gel 124 in the first lane to monitor the electrical field gradient between 122 and 122a. Normally, the gels will all be cast from the same material, so that the field in the first lane should be substantially the same in each of the other lanes 108. For the most part, the fields will be dependent upon the ionic moieties present, which may or may not be affected by the differences in gel concentration in the different lanes. A sample well 126 is formed when casting the gel in the gel mold 102.

The gel plate may be of any convenient size, generally ranging from about 5 to 40 cm in the direction of migration and about 1 to 20 cm normal to the direction of migration, particularly 7.5–15 cm by 12–15 cm. The channels 114 and 114a which communicate with the buffer and the gel will generally have a length of about 0.5 to 3 cm. Conveniently, the angle of the beveled bottom 120 and 120a will generally be from about 20° to 70°.

In FIGS. 3 and 4, the gel plate 100 is set onto gel mold lower plate 104, where plastic blocks 116 and 116a fit onto slots 128 and 128a. At least one of the slots 120 and 120a extend all the way through the plate, so as to leave an opening, exposing the beveled bottom 120 or 120a to the atmosphere. Usually, both slots 120 and 120a are completely opened prior to introducing gel 100 onto gel mold lower plate 104. Lower plate 104 has four pins 130 for registering upper plate 106 in appropriate position in relation to gel plate 100.

Upper plate 106 has a plurality of protrusions 132 which extend into lanes 108 proximal to one end of the lanes to define the sample wells 126. The protrusions are of a size so as to extend not more than about 80% of the thickness of the gel and leave spaces, generally from about 1-2 mm between the dividers 110 and the protrusions 132. With gel at the bottom of the wells, the sample does not leak out of the wells. The spacing allows for air to pass when preparing the gel, thus avoiding air bubble entrapment. Usually, the space between the bottom of the well 126 and the plate 118 will be about 0.5 mm.

In preparing the gels, the gel plate 100 is placed on gel mold lower plate 104, so that the channels 114 and 114a extend down into slots 128 and 128a. The top plate 106, which is conveniently of a semi-hard elastomeric plastic material has four recesses 134 for receiving pins or dowels 130. The top plate 106 is fitted over the lower plate 104 with the recesses 134 in register with the dowels 130 and the protrusions 132 extending into the lanes 108. The bottom 104 and top 106 plates are then locked together, so that the top plate face 136 is in contact with dividers 110, preventing gel from one lane to extend into a second lane. After locking bottom and top plates, 104 and 106 respectively, together with clamps, clips or the like, the plates are then set in vertical position as shown in FIG. 3b. The lanes may then be filed either from the bottom or top.

When filling from the bottom, a manifold 138 is employed having tubes 140 which fit in register with channels 114. At the top of the manifold block are funnels 142, which connect with tubes 140, so that the gel may be introduced into the funnels 142, flow downwardly through tubes 140 into channels 114 and then flow upwardly to fill channels 114a up to or below the level in the manifold 138 to fill the channel and complete the gel. Polymerization of the gel may then be achieved by any convenient activation, such as light, heat, incubation under ambient conditions, or the like, where the course of the polymerization may be monitored by the temperature profile using a temperature sensor, not shown, change in appearance, or the like.

When filling the lanes 108 from above, one can provide for a manifold which can be placed in register with the channels 114a and provide for a porous cover over channels 114, which will allow for air to pass, but prevent passage of the liquid gel. By first filling one row of channels 114 with the gel, the gel may then be added from above without an entrapment. Other techniques may also be used, for producing the gels. In some instances, it may be desirable to provide for various gradients in the gel, providing for areas having different concentrations (% T) and different hardnesses. For example, the portion of the gel immediately downstream from the sample well may comprise a stacking gel, which will have a lower percentage of polymer followed by the resolving gel. By adding different substantially immiscible liquids sequentially, one may obtain a stepped gel having regions of different characteristics.

When the gel is formed, the gel plate 100 may then be placed upon the cooling plate 34 with the blocks 116 and 116a immersed in wells 16 and 18 respectively. Electrodes 144 and 144a are introduced into electrode monitoring the electrical field of the gel in lane 1. Electrode holders 20 and 22 are placed in buffer wells 16 and 18 to provide for the electrical field across the gel.

Figure 6:
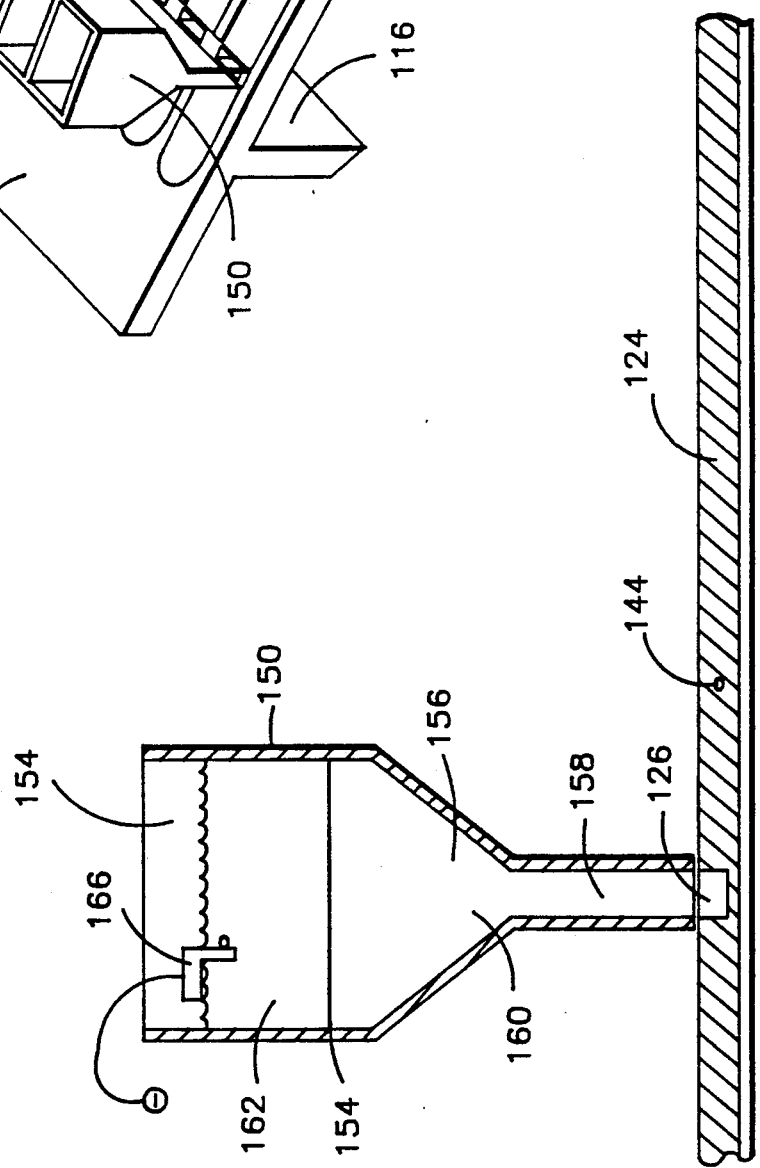
FIG. 6 is a cross-sectional elevational view of the electrophoretic concentrator.

Instead of employing a stacking gel in the lane, the stacking or collecting of the sample components in a single band may be achieved by employing the electrophoretic concentrator 150 as described in FIGS. 6 and electrophoretic concentrator 150 has a block 152 with a plurality of receiving ports 154. The head of the block 152 is funnel shaped, narrowing toward the bottom into a narrowing cross sectional area 156 and into passage 158. The sample 162 is placed on top of the stacking gel 160. A coating of a conductive dye 164 coats the top of the stacking gel 160. A floating electrode 166 is provided which provides an electrical field between the floating electrode 166 and the analyte buffer well electrode 30a. The electrophoretic concentrator is placed directly above the sample wells 126 in gel 124. When conductive dye reaches tap 144 the field is switched to between buffer well electrodes 30 and 30a.

At completion of the electrophoresis, the band components may be transferred from the gel to a membrane or other conventional substrate, employing the equipment depicted in FIG. 8 for the transfer. A stack of sheets are employed having a graphite electrode sheet anode 168 and graphite electrode sheet cathode 168a. Placed above the graphite cathode 168a are paper sheets 170 and 170a soaked with buffer solution. The gel 172 is supported by Netfix substrate 174 for transfer of the bands to a permanent record. For receiving the gel components, membrane 176 is placed in contact with gel 172. Any convenient membrane may be employed, such as Immobilon, nitrocellulose, DBM-nitrocellulose, etc. Above the membrane are placed paper sheets 178 and 178a, which are also soaked with buffer solution. The paper sheets 170, 170a, 178 and 178a allow for transfer of current between the electrodes 168 and 168a.

The package of sheets 180 is placed into a lower electrode frame 182 and then enclosed with upper electrode frame 184. The electrode frames 182 and 184 are connected to a power supply 186, which may also include a timer.

The current is maintained for a sufficient time for transfer of the separated components in the gel to the membrane for further processing and analysis.

A diluter-dispenser device can be provided as a container, for diluting buffer concentrate or other solution to a desired concentration.

The diluter-dispenser device 310 is conveniently made as a molded one piece device with a separate cap 312. The device has a small chamber 314 for receiving the buffer concentrate. A large chamber 316 receives water or other liquid for diluting the concentrate. The diluent is poured into chamber 316 to a predetermined level which is below the top of well 318. The concentrated buffer may then be poured through opening 320 to fill chamber 314 to a designated level. Cap 312 may now be screwed on to threaded channel 322 and the device 310 tipped so as to transfer the concentrated buffer from chamber 314 to the diluent in chamber 316 where it may be mixed by shaking. Once the buffer has been appropriately diluted, it may now be poured from chamber 316 through channel 324 and out pour spout 326.

Having described the various components of the subject system, the use of the system and its various applications will now be considered.

Various gel compositions may be employed to produce the gel matrix. Polyacrylamide, agarose, gelatin, or other agent may be used as a thickening agent for the gel matrix. The gel plate 100 with its plurality of lanes is placed over the lower plate 106 of the gel mold and the channel blocks 108 and 108a seated in slots 128 and 128a. The cover 104 is then placed over the gel plate 100 with the dowels 130 of the lower plate in the recesses 134 and the lower plate 106 and upper plate 104 of the mold held together by clips. The manifold 138 is then placed against the lower plate 104 with the plurality of tubes 140 in register with the channels 114. Suction may be used to pull the gel into the lanes. The components are mixed to form the gel matrix, either at an elevated temperature to lower the viscosity or containing unpolymerized monomer. This composition is then poured into the manifold 138 so as to travel through the lanes 108 and up and out channels 144a. Where the solution has been heated to obtain the desired low viscosity, the solution will be cooled and allowed to gel.

For the most part, with polyacrylamide, the solution will include a chemical or photoinitiator system. Various chemical polymerization systems may be used which are added to the matrix before preparing the plate. For example, TEMED and persulfate may be added to provide polymerization initiation. With the photoinitiator system, the gel composition will be irradiated with light to provide the necessary excitation for polymer initiation and the course of the polymerization followed by employing a thermocouple. Once the temperature becomes stable or approaches ambient temperature, the polymerization may be assumed to be complete. If desired, an acrylamide gradient may be developed by successively adding solutions with increasing amounts of acrylamide and/or cross-linking agent. Alternatively, differential initiation may be used, so as to provide varying degrees of polymerization. In this manner, one may provide for a gel gradient.

In standard PAGE technology, gels commonly range between 5–22.5% T(T=total amount of acrylamide or other gelling agent), mostly between 7.5–15% T. Lower percentages may be employed with linear polyacrylamide. In agarose gel electrophoresis, concentrations between about 0.2–2% T may be employed.

Also, one may provide for a region which is referred to as the stacking gel, having a relatively low acrylamide concentration and a resolving gel having a substantially higher acrylamide concentration. Descriptions of forming gels for gel electrophoresis may be found in *The Practice of Quantitative Gel Electrophoresis,* Chrambach, VCH Publishers. Because of the ability to regulate and monitor the course of the electrophoresis, low concentrations of the gelling agent may be employed.

Depending upon the purpose of the electrophoresis, various buffers may be employed at different pHs, where the gel and the buffers in the buffer wells may conveniently have a common ion. Other components in the gel may include cross linking agents such as BIS, DATD, AcrylAide, etc. Once the gel has been formed filling the lanes and extending through the channels, the mold may be opened and the gel plate released, which is now ready for use.

The buffer wells 16 and 18 are positioned appropriately adjacent to the gel module platform and the gel plate is placed over the gel module with legs extending into the buffer solution in the buffer wells. The electrode holders containing the electrodes are then placed into the buffer solutions to provide the anode and cathode for the anolyte and catholyte solutions to direct the flow of ions and charged sample components. The sensing electrodes are inserted into the holders and extend into the gel in lane one, upon positioning the gel plate on the gel module platform. The sensing electrodes are also connected to the computer.

The sample may now be introduced into the sample well or be concentrated with the electrophoretic concentrator.

The electrophoretic concentrator provides a cone having a stacking gel at the lower portion of the cone with a passage which terminates in an opening substantially coinciding with the sample well. By having a block with a plurality of cones, each with a common stacking gel, each of the wells in the different lanes may receive a sample simultaneously.

Various methods may be used to determine when the sample has reached the well or extended a predetermined distance into the resolving gel. For example, the stacking gel in the cone may be coated with a conductive dye.

The electrode in the electrophoretic concentrator and the electrode in the downstream buffer well provide a voltage gradient across the stacking gel. The upstream electrode in the buffer well is off, while the upstream sensing electrode is on. As the conductive dye moves through the stacking gel and into the resolving gel, the electrical properties between the electrode of the electrophoretic concentrator and the upstream sensing electrode will change. One may employ an additional electrode and use AC current and measure impedance across the gel to sense the band. At a predetermined value, indicating the sample in the resolving gel, the electrode in the upstream buffer well is turned on, creating a voltage gradient across the resolving gel.

The electrode in the sample over the stacking gel may be positioned, so as to float on the surface and to switch off when the electrode contacts the stacking gel.

A conductive dye need not be used, any material which has the desired mobility, so as to stack or precede the components in the sample may be employed. Thus, a fluorescent dye may be detected by the photometer. The photometer may be initially positioned adjacent the sample well, so that a fluorescent dye will provide a signal when it reaches an appropriate site. Once the components of the sample have passed through the stacking gel and into the well and the marker has provided a signal, the stacking gel may be removed and the electrophoresis allowed to proceed.

As the electrophoresis proceeds, the temperature and voltage in the gel is continuously monitored. If the electrophoresis is moving too slowly, the field, e.g., the voltage gradient, may be increased in the gel. Thus, the progress of the electrophoresis is monitored and the progress of the bands slowed or speeded, depending on the satisfactory nature of the separation.

Internal markers may be included in the sample or in control lanes. Derivatives of compounds may be employed, which are fluorescent, which may include proteins, nucleic acids, saccharide or particles. Where one is looking for a known compound, the marker conjugated compound may be used in a control lane.

The photometer can be continuously moved across the gel, moving back and forth with a particular frequency, may occasionally move across the gel, or may be directed to move at particular time intervals. Fluorescence can be provided by using fluorescent standards in a control lane, by providing for fluorescent compounds which bind to the sample components, by providing for compounds in the gel which interact with the sample components to provide fluorescence, or the like. In this manner, the various bands which form in the gel can be monitored, so that the progress of the leading band and the separation between bands can be detected. Conditions can be changed to enhance separation or to stop the electrophoresis, when a desired degree of separation has been achieved.

A diluter-dispenser is provided for diluting buffer concentrate or other reagent, which can be provided as part of the system. A small cup is provided which is filled to a predetermined level, while a mixing container connected to the cup is filled with water or other solution to a predetermined level. By tilting the diluter-dispenser, the concentrate in the cup is transferred to the mixing vessel, where it is diluted and may then be dispensed through the connecting channel in a pour spout into the buffer wells.

Once the electrophoresis is complete, the gels may then be used in a variety of ways. For nucleic acids, various dyes, such as ethidium bromide which intercalates into nucleic acids and is fluorescent, may be employed. After washing away ethidium bromide which is not intercalated, the photometer may be used for detecting the fluorescent bands. Alternatively, a dye in the visible range may be used, e.g., Coomassie blue, and the gel plate may be moved to the light box for viewing the visible bands. If the dye is fluorescent, the photometer module may be removed from the gel module and placed over the light box. The photometer module will feed the fluorescent signals which are observed to the computer. The electroluminescent panel may be employed to detect a dye absorbing in the visible range.

The various signals obtained from the gel module and photometer module are fed to a computer, which interacts with the temperature control and electrodes which provide the voltage gradient and sense the voltage gradient in the gel. A keyboard is provided which interacts with the computer so that the variables may be changed in accordance with the performance of the electrophoresis and the desires of the operator. The conditions of the electrophoresis may be monitored with a CRT and hard copies of the conditions and band separations may be made with a printer connected to the computer. By employing lanes having different levels of thickener or polymer, Ferguson plots may be developed which are characteristic for a particular compound, e.g., protein, (characterization in respect to size and charge).

A program is provided which relates the various signals obtained from the gel module and the photometer module to the course of the electrophoresis and maintains constant conditions in the gel as to temperature and electrical gradient by modifying the voltage at the electrodes in the buffer wells and the rate of cooling provided by the cooling system.

While the gels may be analyzed directly, in many situations, one may wish to transfer the separated molecules from the gel onto a membrane For this purpose, one removes the gels from the lanes onto a porous substrate, such as Netfix, or the like. A stack of sheets are provided, where the gels are sandwiched between papers wetted with buffer, which are in turn sandwiched between sheet electrodes. By introducing an electrode frame attached to a power supply, the components in the gel may be transferred to the membrane and covalently or non-covalently bonded to the membrane. The sample components may then be probed, with antibodies, nucleic acid probes, or the like.

The subject system may be used not only for electrophoresis, but also for isoelectric focusing in carrier ampholyte or immobilized pH gradient gels. Steady-state conditions may be monitored directly using fluorescent propidium iodide markers.

The system requires only a small power supply, for example, providing 0–500V±10% at currents of 0–25 milliamps, usually providing independent regulation of voltage and current. The cooling system has a capacity to remove heat at a rate of about 0–200 BTU/hr with a precision of about ±0.1° C.

The system can be used for detecting and characterizing a wide variety of sample components. The system may be used to monitor food, detecting viruses, diagnosing diseases, such as the production of isozymes as occurs in myocardial infarction, typing, as to major histocompatibility complex antigens, blood type, or the like, detecting sugars, lipid complexes, etc. For sugars, it may be convenient to form boronates, where the boron may be attached to a charged molecule, such as polyphosphate, polyacrylate, etc. Because of the reproducibility of the system, the ability to carry out a plurality of lanes under the same conditions, so that lanes with known substances may be employed, accurate determinations of components in a sample can be made.

It is evident from the above description, that a convenient total electrophoretic system is provided which allows the user the ability to prepare its own gels or buy them preformed, carry out electrophoresis in an efficient and reproducible manner under controlled conditions and then use the gels in accordance with known procedures for specifically determining the particular components of the sample. In addition, a stacking gel is provided separate from the gel plate, which allows for substantial concentration of the components of the sample, further improving the efficiency of separation.

All publications and patent applications cited in this specification are herein incorporated by reference as if each individual publication or patent application were specifically and individually indicated to be incorporated by reference.

Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims.

What is claimed is:

1. A gel electrophoresis system for separating components of a mixture by their physical and chemical characteristics by passage through a gel under a voltage gradient, said system comprising:
   a. a gel plate comprising:
      a surface for supporting a gel;
      orifices proximal to each of the ends of said surface; and
      channels communicating with said orifices and extending downwardly from said surface for introduction into buffer solution;
   b. a housing comprising a gel electrophoresis module, a photometer module, and electrical circuitry for external connection;
   c. said gel electrophoresis module comprising:
      a temperature control platform for supporting said gel plate;
      means for cooling said platform;
      buffer wells for containing buffer solution on opposite sides of said temperature control platform;
      electrodes for creating a voltage gradient across said gel plate when positioned in said buffer wells; and
      a pair of sensing electrodes for monitoring the voltage gradient across a gel on said gel surface;
   d. said photometer module comprising:
      a cover housing for fitting over said gel module;
      a carriage mounted in said housing;
      means for moving said carriage across said housing;
      a photometer mounted on said carriage and comprising:
         at least two photodetectors;
         a pair of filters having different wave length ranges, each photodetector having one of the filters in the light path to said photodetector; and
         a pair of optical fibers for receiving light and transmitting light to each of said photodetectors through said filters;
      an excitation light source;
   e. electrophoretic concentrating means comprising:
      a manifold comprising a plurality of vessels for containing a stacking gel terminating in a narrow passageway; and
      at least one floating electrode for detecting the height of a solution above said stacking gel;
   f. monitoring and regulating means operatively connected to said electrical circuitry, said monitoring and regulating means comprising:
      means for receiving and analyzing signals from said photodetectors and determining the wave length range of light and intensity of light received by said optical fibers;
      means for detecting a sample component band in said gel by means of said wave length and intensity determination;
      means for determining the location of said band by means of said sample component band detecting means and the location of said carriage;
      means for determining the temperature of said platform and/or gel;
      means for determining the voltage gradient in said gel; and
      means for controlling said temperature and said voltage gradient in said gel in response to a defined program.

2. A system according to claim 1, wherein said gel plate comprises a plurality of lanes and a plurality of channels at each end, said system further comprising:
   a gel mold for producing gels with said gel plate, said gel mold comprising:
      a bottom form having open slots for receiving said channels;
      a top form having a flat face with aligned spaced apart protuberances to form sample wells in said gel;
      means for aligning said top and bottom forms and holding them in register; and
   a gel filling manifold comprising a block having a plurality of gel receiving openings on an upper edge; and
   a plurality of passageways extending from said gel receiving openings through said block and out a wall of said block in alignment for registry with said channels, wherein the height of said passageways is at least equal to the length of said lanes.

3. A system according to claim 1, wherein said gel plate comprises a plurality of lanes and a plurality of orifices proximal to each end, and said photometer module comprises two photodetectors per lane.

4. A system according to claim 3, wherein said channels terminate in a beveled edge.

5. A gel plate comprising:
   a surface for supporting a gel with a plurality of dividers defining a plurality of lanes;
   orifices proximal to each of the ends of said lanes; and channels communicating with said orifices and extending downwardly from said surface for introduction into buffer solution and terminating in beveled edges.

6. A gel plate according to claim 5, further comprising a pair of spaced apart passageways along one side of said surface for receiving sensing electrodes.

7. A gel plate according to claim 5, wherein said plate is a clear plastic.

8. An electrophoretic concentrator comprising:
a manifold comprising a plurality of vessels for containing a stacking gel terminating in a narrow passageway;
a stacking gel in each of said vessels extending only a portion of the height of said vessels; and
at least one electrode for providing a field through said stacking gel.

9. An electrophoretic concentrator according to claim 8, further comprising a conductive dye coat on said stacking gel.

10. An electrophoretic concentrator according to claim 8, wherein said vessels are in part square tubular shaped.

11. A gel mold system for producing a gel for gel electrophoresis in a plurality of lanes, said system comprising:
a bottom form having open slots for receiving a group of channels;
a top form having a flat face with aligned spaced apart protuberances to form sample wells in said gel;
means for aligning said top and bottom forms and holding them in register; and
a gel filling manifold comprising a block having a plurality of gel receiving openings on an upper edge; and
a plurality of passageways extending from said openings through said block and out a wall of said block in alignment for registry with said channels, wherein the height of said passageways is at least equal to the length of said lanes.

* * * * *